(12) United States Patent
Rahn et al.

(10) Patent No.: US 6,316,680 B1
(45) Date of Patent: Nov. 13, 2001

(54) ISOLATION OF α-ETHYNYL CARBINOLS BY DISTILLATION

(75) Inventors: Ralf-Thomas Rahn, Mannheim; Harald Rust, Neustadt; Thomas Rühl, Frankenthal; Jochem Henkelmann, Mannheim; Susanne Stutz, Weinheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/455,161

(22) Filed: Dec. 6, 1999

(30) Foreign Application Priority Data

Dec. 8, 1998 (DE) ................................ 198 56 592

(51) Int. Cl.$^7$ ..................... C07C 27/26; C07C 33/04; C07C 27/00
(52) U.S. Cl. ................... 568/913; 568/874; 568/876; 568/879
(58) Field of Search ................... 568/874, 876, 568/879, 913

(56) References Cited

U.S. PATENT DOCUMENTS

| 3,576,889 | 4/1971 | Martin et al. | 260/638 |
| 4,320,236 | 3/1982 | Wiederkehr | 568/813 |

FOREIGN PATENT DOCUMENTS 642936   5/1984   (CH) .

*Primary Examiner*—Johann Richter
*Assistant Examiner*—J. Parsa
(74) *Attorney, Agent, or Firm*—Herbert B. Keil

(57) ABSTRACT

In a process for isolating α-ethynyl carbinols from the liquid reaction mixture from the addition of acetylene onto α,β-unsaturated carbonyl compounds by distillation, the distillation is carried out continuously, the feed stream is introduced into the middle section of a distillation column (K), the major part of the water is distilled off azeotropically together with the solvent at the top of the column, and the α-ethynyl carbinol target product is taken off below the feed point to the column.

12 Claims, 2 Drawing Sheets

ISOLATION OF α-ETHYNYL CARBINOLS BY DISTILLATION

The present invention relates to a process for isolating α-ethynyl carbinols from the liquid reaction mixture from the addition of acetylene onto α,β-unsaturated carbonyl compounds by distillation, and also a use of the process for the isolation of vinylbutynol.

α-Ethynyl carbinols are addition products of acetylene onto α,β-unsaturated carbonyl compounds. In order to reduce the tendency of the carbonyl compound to polymerize during the addition reaction, alkali metal acetylides or alkaline earth metal acetylides are generally used as reagent at a low temperature in a dipolar aprotic solvent. Thus, it has been found to be usefull to use a mixed sodium-magnesium acetylide complex or lithium acetylide. The lithium acetylide complex can either be prepared directly in an ether, in which case the additional use of a complexing agent, for example dimethyl sulfoxide or dimethylacetamide, as described in U.S. Pat. No. 3,576,889, is advisable, or the lithium acetylide is prepared in liquid ammonia and the ammonia is subsequently replaced by an ether, corresponding to the process proposed in CH-A-642 936. The reaction with the carbonyl compound is carried out at low temperatures; CH-A-642 936 recommends temperatures in the range from −30 to 20° C., preferably from −20 to 10° C. After the addition reaction, the resulting α-ethynyl carbinolate is hydrolyzed. To work up the product mixture on a laboratory scale, CH-A-642 936 describes drying of the ether phase using sodium sulfate and subsequent distillation using a Vigreux column.

Processes for working up the product mixture from the addition reaction of acetylene onto α,β-unsaturated carbonyl compounds on an industrial scale are not known to date. Problems are firstly the high hazard potential (the decomposition energy of α-ethynyl carbinols is above 1000 J/g) and secondly the recovery of α-ethynyl carbinols from water-containing mixtures, since α-ethynyl carbinols generally distill off together with water as heteroazeotropes which do separate into two phases but with only a slightly different composition.

In the case of batch distillations, as are described, for example, in CH-A-642 936, there is also an increased hazard potential due to the accumulation of the easily decomposed α-ethynyl carbinols in the bottom of the column.

It is an object of the present invention to provide an industrial-scale, continuous distillation process for isolating α-ethynyl carbinols, which has good economics and ensures a high level of safety when carrying out the process.

We have found that this object is achieved in a process for isolating α-ethynyl carbinols from the liquid reaction mixture from the addition of acetylene onto α,β-unsaturated carbonyl compounds by distillation by a) carrying out the distillation continuously,
b) introducing the feed stream in the middle section of a distillation column,
c) azeotropically distilling off the major part of the water with solvent at the top of the column and
d) taking off the target product α-ethynyl carbinol below the feed point to the column.

It has been found that the major part of the water in the liquid reaction mixture from the addition of acetylene onto α,β-unsaturated carbonyl compounds can be removed azeotropically together with the solvent at the top of the distillation column, thus solving the problem of the separation of the water/α-ethynyl carbinol azeotrope which cannot be carried out directly.

In the addition reaction with acetylene, it is possible in principle to use any α,β-unsaturated carbonyl compound of the formula

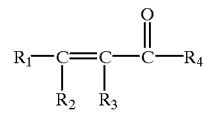

where $R_1$ and $R_4$ are each hydrogen or an unbranched or singly or multiply branched aliphatic $C_1$–$C_{10}$-radical or an unsubstituted or singly or multiply aliphatically substituted alicyclic $C_3$–$C_{10}$-radical or $R_1$ and $R_4$ are together an aliphatic $C_1$–$C_4$-radical which joins both parts of the molecule and $R_2$ and $R_3$ are each hydrogen or an aliphatic $C_1$–$C_3$-radical. Preference is given to using acrolein, methyl vinyl ketone, mesityl oxide, β-ionone, pseudoionone, citral or cyclopentenone as α,β-unsaturated carbonyl compounds.

The addition reaction is carried out in a known manner, using an alkali metal acetylide or alkaline earth metal acetylide as reagent at low temperature in a dipolar aprotic solvent. For example, a mixed sodium-magnesium acetylide complex or lithium acetylide can be used. The lithium acetylide complex can be prepared in a known manner either directly in an ether, in which case additions of a complexing agent such as dimethyl sulfoxide, dimethylacetamide or dimethylformamide are advisable, or the lithium acetylide is prepared in liquid ammonia and the ammonia is subsequently replaced by an organic solvent, in particular by an ether. Organic solvents suitable for carrying out the present work-up process are all those which form an azeotrope with water that has a boiling point which is at least 5° C., preferably at least 10° C., lower than that of the α-ethynyl carbinol or that of the azeotrope of the α-ethynyl carbinol with water. These include, in particular, ethers such as diethyl ether, tetrahydrofuran or isopropyl ether and also aliphatic, cycloaliphatic or aromatic hydrocarbons, for example pentane, cyclohexane or toluene, and alcohols, in particular butanol.

A typical reaction mixture from the addition of acetylene onto α,β-unsaturated carbonyl compounds has the following composition:

| | |
|---|---|
| α-ethynyl carbinol: | from 2 to 40% by weight, preferably from 5 to 20% by weight, |
| water: | from 0.1 to 10% by weight, preferably from 1 to 5% by weight, |
| high boilers: | from 0 to 5% by weight, |
| intermediate boilers: | from 0 to 2% by weight, |
| balance: | solvent. |

High boilers with reference to the present invention are oligomers and polymers of the α,β-unsaturated carbonyl compound; they have virtually no vapor pressure.

Intermediate boilers are predominantly substances having a boiling point which is above the boiling point of the respective α-ethynyl carbinol. Intermediate boilers can be, for example, by-products which are formed by reaction of the α,β-carbonyl compound with the α-ethynyl carbinol.

In the process of the present invention, the liquid reaction mixture from the addition of acetylene onto α,β-unsaturated carbonyl compounds is fed continuously into the middle section of a distillation column, i.e. the distillation column used according to the present invention has a stripping section.

The target product α-ethynyl carbinol is taken off below the feed point to the column. If the purity requirements are only moderate or if the levels of intermediate and high boilers to be separated off are low, the target product can be taken off at the bottom. However, the target product is generally taken off at a side offtake, preferably at the second to fifth theoretical plate, counted from the bottom.

The distillation column is essentially not subject to any restrictions in respect of construction. In principle, it is possible to use any vacuum distillation column, with preference being given to columns having separation-active internal fittings in the form of structured packing. Particular preference is given to columns which have structured packing in the middle and lower sections and in their upper section have trays, preferably from two to three trays; a droplet precipitator can be provided at the top of the column. Particularly in the case of small boiling point differences between the solvent/water azeotrope and the α-ethynyl carbinol/water azeotrope, the distillation column can also be configured as a dividing wall column.

The preferred operating conditions for the distillation column are:
pressure: from 10 mbar to 1 bar absolute, preferably from 100 to 700 mbar, number of theoretical plates: from 5 to 50, preferably from 7 to 20, particularly preferably from 8 to 15.

In order to be able to carry out condensation using cooling water, it is advantageous to reduce the pressure at the top of the distillation column only so far that the condensation temperature at the top does not go below about 35° C. If, for example, methyl tert-butyl ether is used as solvent, a pressure of about 500 mbar is set at the top. At the top of the distillation column, the major part of the water in the liquid reaction mixture is distilled off azeotropically together with the solvent.

It is advantageous to use solvents which form a heteroazeotrope with water, i.e. form a azeotrope which separates into two phases having different compositions after condensation. In this case, the top product is, after condensation, fed to a phase separator and the organic phase or part thereof is returned as runback to the distillation column.

The feed to the phase separator is preferably undercooled, by which means the solubility of the water in the organic phase is reduced and improved removal of water is thus achieved.

According to the present invention, the target product α-ethynyl carbinol is taken off below the feed point to the column. In general, the target product α-ethynyl carbinol is taken off via a side offtake on the distillation column. High boilers and intermediate boilers, together with small amounts of α-ethynyl carbinol, are then obtained at the bottom of the column. Very little target product should be lost in the bottoms. However, owing to the ease with which the α-ethynyl carbinols decompose, it is necessary to avoid exceeding a maximum temperature which is generally about 50 kelvin below the decomposition onset temperature. For example, pure vinylbutynol decomposes above about 170° C. with an energy release of about 2000 J/g. At a residence time in the order of hours, the bottom temperature is limited to a maximum of 100° C. while at a residence time in the order of minutes it is restricted to a maximum of 120° C.

In a preferred variant of the process, a prevaporizer which is operated at reduced pressure, preferably at a pressure of from 10 mbar to 1 mbar absolute, particularly preferably from 100 to 700 mbar, is installed upstream of the distillation column. The operating pressure of the prevaporizer is limited for the same reasons as have been discussed above in respect of the bottom of the distillation column, taking into account the ease of decomposition of the α-ethynyl carbinols. To avoid decomposing the product, prevaporizers operating by the falling film principle or particularly preferably thin film vaporizers (i.e. apparatuses having low residence times) are used. The thin film vaporizer is operated preferably in cocurrent, i.e. the vapor is taken off at the lower end of the apparatus in the vicinity of the outlet for the bottoms containing the high boilers. In this mode of operation, the residual α-ethynyl carbinol content in the high-boiling residue is lower than when the prevaporizer is operated in countercurrent.

Since the target product, namely α-ethynyl carbinol, is also taken off at the bottom of the distillation column owing to the temperature limitation necessary because of its thermal instability, it is advantageous to recirculate the bottoms to the prevaporizer. The process of the present invention is advantageously used for the isolation of vinylbutynol. In the isolation of vinylbutynol, a bottom product comprising about 75% by weight of vinylbutynol and about 25% of intermediate boilers, for example, is obtained at a column pressure of 500 mbar. At about 2% by weight of intermediate boilers and about 18% by weight of vinylbutynol in the feed to the distillation column, about 33% of the vinylbutynol is lost as a result. The loss of target product can, as indicated above, be limited by recirculating the bottoms to the prevaporizer.

BRIEF DESCRIPTION OF DRAWINGS

The invention is illustrated below with the aid of examples and a drawing. In the drawing FIG. 1 schematically shows a first example of a process according to the present invention and FIG. 2 schematically shows a second preferred example of a process according to the present invention.

A first example is described below in conjunction with FIG. 1:

Figure 1:
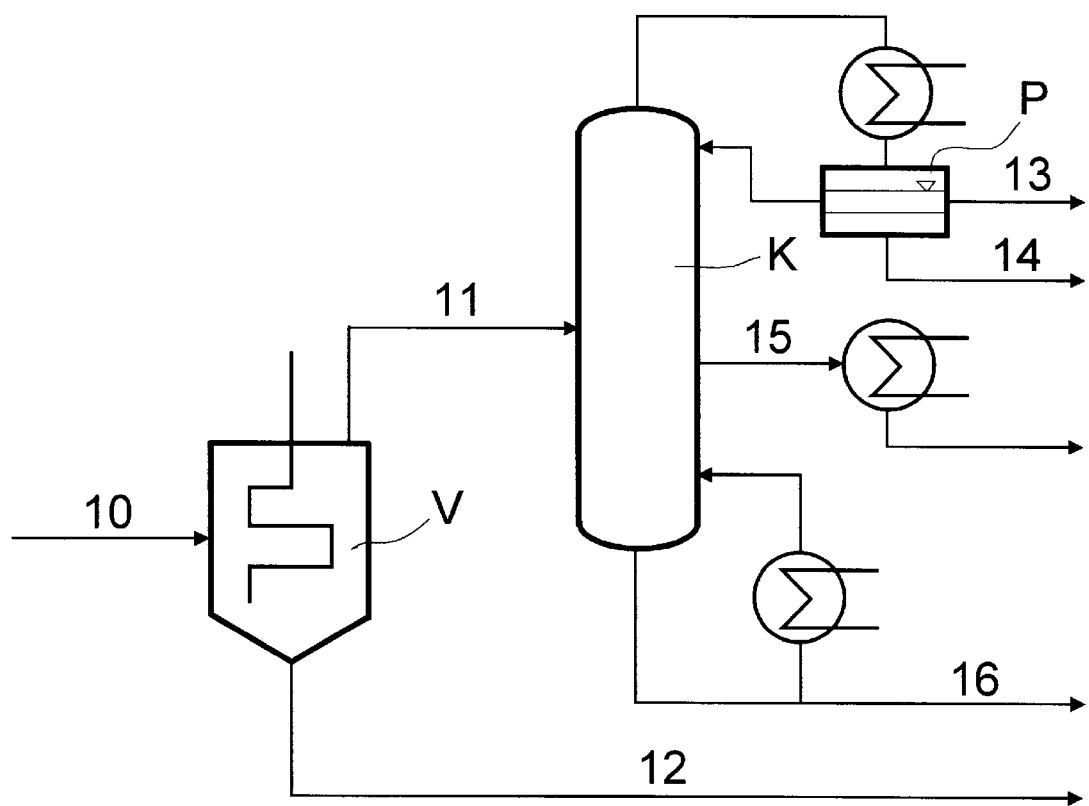

400 g/h of a liquid reaction mixture obtained from the addition of acetylene onto methyl vinyl ketone and having a composition of 78% of methyl tert-butyl ether as solvent (hereinafter abbreviated as MTBE), 17% of vinylbutynol target product (hereinafter abbreviated as VBI), 3% by weight of water, and 2% by weight of intermediate and high boilers were fed to a thin film evaporator V which was operated in cocurrent at an oil bath temperature of 130° C. and a pressure of 500 mbar absolute. From the bottom of the evaporator, 10 g/h of high boilers were discharged (stream 12) and the vapor (stream 11) was fed to the fifth theoretical plate of a distillation column K containing structured, metal mesh packing and having 10 theoretical plates with a phase separator P at the top and a side offtake for vapor at the third theoretical plate (stream 15) downstream of which a condenser was located. The distillation column K was operated at a pressure at the top of 500 mbar absolute and a temperature at the top of 33° C. The condensed vapor was fed to a phase separator (P). The denser aqueous phase (stream 14) was taken off and the organic phase, which consisted essentially of pure MTBE containing about 1.5% by weight of dissolved water, was returned to the column at a ratio of 5:1. A distillate stream of 322 g/h of water-saturated MTBE (stream 13) and 6 g/h of MTBE-saturated water (stream 14) were taken off. At a temperature in the side offtake of 100° C., 62 g/h of vinylbutynol (stream 15) having a composition of 99% by weight of vinylbutynol, 1% by weight of MTBE and 150 ppm of intermediate boilers were taken off in vapor form and passed to a condenser.

At the bottom of the column, 5 g/h of vinylbutynol-containing high boiler mixture were taken off at 107° C. and discharged (stream 16). The total amount of high boilers discharged (sum of streams 12 and 16) was about 15 g per hour. 62 g/h of vinylbutynol were obtained, i.e. the distillation yield of vinylbutynol was 91.2%.

The compositions of streams 10 to 16 are shown in Table 1 below:

TABLE 1

| | Stream No. | | | | | |
|---|---|---|---|---|---|---|
| | 10 | 11 | 12 | 13 | 14 | 15 | 16 |
| Mass flow (g/h) | 400 | 390 | 10 | 322 | | 62 | 5 |
| Proportion by mass | | | | | | | |
| MTBE | 0.78 | 0.80 | 0.09 | 0.985 | 0.02 | 0.01 | 26 ppm |
| H$_2$O | 0.03 | 0.03 | 0.01 | 0.015 | 0.98 | 18 ppm | <1 ppm |
| VBI | 0.17 | 0.17 | 0.09 | <1 ppm | <1 ppm | 0.99 | 0.70 |
| HB | 0.02 | <1 ppm | 0.77 | <1 ppm | <1 ppm | <1 ppm | 18 ppm |
| IB | <0.01 | <0.01 | 0.04 | <1 ppm | <1 ppm | 150 ppm | 0.30 |

TABLE 2

Figure 2:
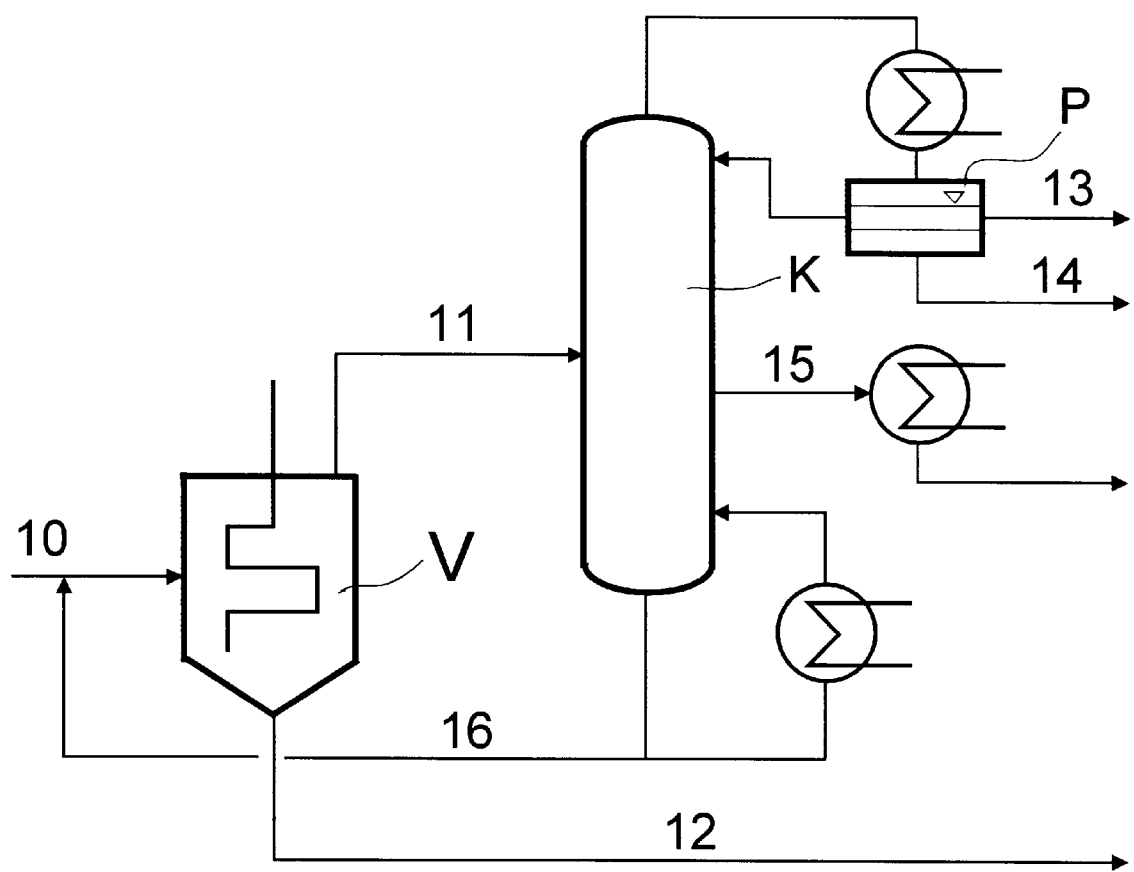

| | Stream No. | | | | | |
|---|---|---|---|---|---|---|
| | 10 | 11 | 12 | 13 | 14 | 15 | 16 |
| Mass flow (g/h) | 400 | 414 | 12 | 322 | | 66 | 26 |
| Proportion by mass | | | | | | | |
| MTBE | 0.78 | 0.75 | 0.08 | 0.985 | 0.02 | 0.01 | 22 ppm |
| H$_2$O | 0.03 | 0.03 | 0.01 | 0.015 | 0.98 | 17 ppm | <1 ppm |
| VBI | 0.17 | 0.20 | 0.10 | <1 ppm | <1 ppm | 0.99 | 0.70 |
| HB | 0.02 | <1 ppm | 0.65 | <1 ppm | <1 ppm | <1 ppm | 4 ppm |
| IB | <0.01 | 0.02 | 0.16 | <1 ppm | <1 ppm | 481 ppm | 0.30 | where MTBE = methyl tert-butyl ether
VBI = vinylbutynol
HB = high boilers
IB = intermediate boilers Example 2 is described below in conjunction with FIG. 2

400 g/h of the reaction mixture obtained from the reaction of acetylene with methyl vinyl ketone and having a composition of 78% of MTBE, 17% by weight of VBE, 3% by weight of water and 2% by weight of intermediate boilers were fed to a thin film evaporator (V) (stream 10). In steady-state operation, 30 g/h of the stream from the distillation column (K) (stream 16) were fed to the thin film evaporator V in addition to the abovementioned feed stream. The thin film evaporator V was operated in cocurrent at an oil bath temperature of 130° C. and a pressure of 500 mbar absolute. 12 g/h of high boilers (stream 12) were discharged from the bottom of the vaporizer. The vapor was condensed and pumped to the fifth theoretical plate of a distillation column K which had 10 theoretical plates and was equipped at the top with a phase separator P and at the third theoretical plate had a side offtake for vapor. A condenser was installed downstream of the side offtake. The distillation column K was operated at a pressure at the top of 500 mbar absolute and the temperature at the top was 33° C. The condensed vapor was fed to a phase separator P from which the denser aqueous phase (stream 14) was discharged. The organic phase consisting of virtually pure MTBE with about 4% by weight of water was returned to the column in a ratio of 5:1. A distillate stream of 322 g/h of water-saturated MTBE (stream 13) and 6 g/h of MTBE-saturated water (stream 14) were taken off. At a temperature in the side offtake of 100° C., 66 g/h of VBI (stream 15) having a composition of 99% by weight of VBI, 1% by weight of MTBE and 481 ppm of intermediate boilers were taken off in vapor form and passed to a condenser. At the bottom of the column, a vinylbutynol-containing high boiler mixture (stream 16) was taken off at 107° C. and was recirculated to the evaporation stage. With recirculation of the high boiler stream from the distillation to the prevaporizer, the amount of high boilers discharged was only 12 g/h. 66 g/h of vinylbutynol target product were obtained. The distillation yield of vinybutynol was 97.1%.

We claim:

1. A process for isolating α-ethynyl carbinols from the liquid reaction mixture from the addition of acetylene onto α,β-unsaturated carbonyl compounds by distillation, which comprises
   a) carrying out the distillation continuously,
   b) introducing the feed stream (11) in the middle section of a distillation column (K),
   c) azeotropically distilling off the major part of the water with the solvent at the top of the column and
   d) taking off the target product α-ethynyl carbinol below the feed point (11) to the column.

2. The process of claim 1, wherein the α-ethynyl carbinol target product is taken off at a side offtake.

3. The process of claim 1, wherein the operating parameters of the distillation column (K) are as follows:
   pressure: from 10 mbar to 1 bar absolute,
   number of theoretical plates: from 5 to 50.

4. The process of claim 1, wherein the top product from the distillation column (K) is fed to a phase separator (P) and the organic phase or part thereof is returned as runback to the distillation column (K).

5. The process of claim 4, wherein the feed to the phase separator (P) is undercooled.

6. The process of claim 1, wherein the prevaporizer (V) which is operated under reduced pressure, is installed upstream of the distillation column.

7. The process of claim 6, wherein the prevaporizer (V) is a thin film evaporator.

8. The process of claim 7, wherein the thin film evaporator is operated in cocurrent.

9. The process of claim 6, wherein the bottoms (16) from the distillation column (K) are recirculated to the prevaporizer (V).

10. The process of claim 1, in which isolated α-ethynyl carbinol is vinyl butanol.

11. The process of claim 1, wherein the operating parameters of the distillation column (K) are as follows:
    pressure: from 100 mbar to 700 mbar,
    number of theoretical plates: from 8 to 15.

12. The process of claim 1, wherein a prevaporizer (V) which is operated at a pressure of from 10 mbar to 1 bar absolute is installed upstream of the distillation column.

* * * * *